(12) United States Patent
Park

(10) Patent No.: US 12,165,750 B2
(45) Date of Patent: Dec. 10, 2024

(54) SYSTEM AND METHOD FOR COLLECTING CLINICAL TRIAL DATA BASED ON BLOCK-CHAIN

(71) Applicant: JNPMEDI INC., Seoul (KR)

(72) Inventor: Young Yong Park, Incheon (KR)

(73) Assignee: JNPMEDI INC., Seoul (KR)

( * ) Notice: Subject to any disclaimer, the term of this patent is extended or adjusted under 35 U.S.C. 154(b) by 276 days.

(21) Appl. No.: 17/573,248

(22) Filed: Jan. 11, 2022

(65) Prior Publication Data
US 2022/0270717 A1  Aug. 25, 2022

(30) Foreign Application Priority Data
Feb. 23, 2021  (KR) .......... 10-2021-0024092

(51) Int. Cl.
| | |
|---|---|
| *G16H 10/20* | (2018.01) |
| *G06N 5/01* | (2023.01) |
| *H04L 9/32* | (2006.01) |
| *H04L 9/00* | (2022.01) |

(52) U.S. Cl.
CPC .......... *G16H 10/20* (2018.01); *G06N 5/01* (2023.01); *H04L 9/3239* (2013.01); *H04L 9/50* (2022.05)

(58) Field of Classification Search
CPC ........ G16H 10/20; G16H 10/60; G16H 50/20; G06N 5/01; H04L 9/3239; H04L 9/50; H04L 63/123; H04L 9/0861; H04L 2209/88
See application file for complete search history.

(56) References Cited

U.S. PATENT DOCUMENTS

| | | | | |
|---|---|---|---|---|
| 2008/0256128 A1* | 10/2008 | Pierce | .............. | G16H 15/00 |
| 2008/0270177 A1* | 10/2008 | Chamberlain | ......... | G16H 30/20 |
| | | | | 705/2 |
| 2015/0161358 A1* | 6/2015 | Meshkin | ............... | G16H 10/20 |
| | | | | 705/2 |

(Continued)

FOREIGN PATENT DOCUMENTS

| | | |
|---|---|---|
| KR | 10-2010-0092557 A | 8/2010 |
| KR | 10-1438450 B1 | 9/2014 |

(Continued)

OTHER PUBLICATIONS

Olivia Choudhury et al., "A Blockchain Framework for Ensuring Data Quality in Multi-Organizational Clinical Trials," 2019, pp. 1-9. (Year: 2019).*

(Continued)

*Primary Examiner* — Christopher J Brown
*Assistant Examiner* — Canh Le
(74) *Attorney, Agent, or Firm* — Bridgeway IP Law Group, PLLC; Sang Ho Lee; Hyun Woo Shin

(57) ABSTRACT

Provided is a method and system for collecting clinical trial data based on blockchain, and the method of collecting clinical trial data based on blockchain includes the steps of: receiving the clinical trial data from a researcher terminal; requesting verification of the received clinical trial data from a verification node; performing consensus verification on a verification result when the verification result according to the verification request is received from the verification node; and propagating the clinical trial data to the verification node according to a result of the consensus verification, performed by a platform.

15 Claims, 3 Drawing Sheets

(56) References Cited

U.S. PATENT DOCUMENTS

| | | | |
|---|---|---|---|
| 2018/0218779 A1* | 8/2018 | Collins, Jr. | H04L 9/3247 |
| 2019/0327097 A1* | 10/2019 | Tang | H04L 67/60 |
| 2020/0160943 A1 | 5/2020 | Ueno et al. | |
| 2021/0091957 A1* | 3/2021 | Ford | H04L 67/10 |
| 2021/0111900 A1* | 4/2021 | Inokuchi | H04L 9/3239 |
| 2023/0207072 A1* | 6/2023 | Kim | H04L 9/3242 380/44 |

FOREIGN PATENT DOCUMENTS

| | | | |
|---|---|---|---|
| KR | 2020-0067636 A | 6/2020 | |
| KR | 10-2164156 B1 | 10/2020 | |
| WO | 2020/079492 A1 | 4/2020 | |

OTHER PUBLICATIONS

Taras Maksymiv, "Ways of Unauthorized Access to Medical Data and Approach to Organize Secure Access using Blockchain Technology," 2020, pp. 791-795 (Year: 2020).*

Mohammad Saidur Rahman et al., "A Novel Architecture for Tamper Proof Electronic Health Record Management System using Blockchain Wrapper", 2019 ACM International Symposium on Blockchain and Secure Critical Infrastructure, 2019. Jul. 8, 2019, Auckland, New Zealand.

Zonyin Shae et al.,"On the Design of a Blockchain Platform for Clinical Trial and Precision Medicine", 2017 IEEE 37th International Conference on Distributed Computing Systems, pp. 1972-1980.

Ilhaam A.Omar et al.,"Applications of Blockchain Technology in Clinical Trials: Review and Open Challenges". Arabian Journal for Science and Engineering (2021), vol. 46, No. 4, pp. 3001-3015.

Korean Intellectual Property Office, "Request for Submission of an Opinion" for counterpart Korean patent application No. 10-2021-0024092, issued on Oct. 25, 2023.

* cited by examiner

SYSTEM AND METHOD FOR COLLECTING CLINICAL TRIAL DATA BASED ON BLOCK-CHAIN

CROSS-REFERENCE TO RELATED APPLICATION(S)

The application claims benefit of priority to Korean patent application No. 10-2021-0024092 filed on Feb. 23, 2021, the disclosure of which is hereby incorporated by reference in its entirety.

BACKGROUND OF THE INVENTION

Field of the Invention

The present invention relates to a system and method for collecting clinical trial data based on blockchain, and more specifically, to a system and method for collecting highly reliable clinical trial data that cannot be forged/falsified.

Background of the Related Art

As interest in health increases in modern society, the number of clinical trials for development of new medicines is rapidly increasing. Recently, case report forms (CRFs) used for clinical trials are electronically filed more and more, and many studies are conducted to derive highly reliable clinical trial results.

Accordingly, electronic case record sheet (eCRF) systems for increasing validity and reliability in collecting clinical trial data are provided. However, since the conventional electronic case record systems are constructed as a single system, there is a limit in fundamentally preventing forgery/falsification, such as a risk of manipulating records inside a system or being exposed to a hacking attack from the outside of the system.

Therefore, a system and method for fundamentally preventing forgery/falsification, which may occur in the process of collecting clinical trial data, and collecting highly reliable clinical trial data is required.

SUMMARY OF THE INVENTION

Accordingly, the present invention has been made in view of the above-mentioned problems occurring in the prior art, and it is an object of the present invention to provide a system and method for collecting highly reliable clinical trial data that cannot be forged/falsified on the basis of blockchain.

To accomplish the above object, according to an aspect of the present invention, there is provided a method of collecting clinical trial data based on blockchain, the method comprising the steps of: receiving the clinical trial data from a researcher terminal; requesting verification of the received clinical trial data from a verification node; performing consensus verification on a verification result when the verification result according to the verification request is received from the verification node; and propagating the clinical trial data to the verification node according to a result of the consensus verification.

In addition, the method of collecting clinical trial data may further comprise, before the step of requesting verification of the received clinical trial data, the step of setting a verification rule of the clinical trial data and distributing the verification rule to the verification node.

Meanwhile, the verification rule may include an ID of a case report form and an ID and data value of data to be input as an input value of the clinical trial data, and include one-way encryption information of the input data as an output value of the clinical trial data.

In addition, the verification node may verify the clinical trial data by executing the distributed verification rule, and return a result of the verification.

Meanwhile, the verification result may include one-way encryption information of encrypting the clinical trial data only when the clinical trial data is valid.

In addition, the step of performing consensus verification may verify validity of the one-way encryption information according to the verification result using a blockchain consensus algorithm.

According to another embodiment of the present invention, there is provided a system for collecting clinical trial data based on blockchain, the system comprising: a data receiving unit for receiving the clinical trial data from a researcher terminal; a verification request unit for requesting verification of the clinical trial data by sending the received clinical trial data to one or more verification nodes; a consensus verification unit for performing consensus verification on a verification result when the verification result is received from the one or more verification nodes; and a data collection unit for propagating a consensus-verified clinical trial data.

In addition, the system for collecting clinical trial data based on blockchain may further comprise a verification rule setting unit for setting a verification rule of the clinical trial data and distributing the verification rule to the one or more verification nodes.

Meanwhile, the verification rule may include an ID of a case report form and an ID and data value of data to be input as an input value of the clinical trial data, and include one-way encryption information of the input data as an output value of the clinical trial data.

In addition, the one or more verification nodes may include: a verification execution unit for verifying the clinical trial data by executing the distributed verification rule; and a verification result return unit for returning a verification result of the clinical trial data.

Meanwhile, the verification result may include one-way encryption information of encrypting the clinical trial data only when the clinical trial data is valid.

In addition, the consensus verification unit may perform consensus verification by confirming validity of the one-way encryption information according to the verification result using a blockchain consensus algorithm.

According to the present invention, when clinical trial data is input, verification is performed through a verification node that forms a blockchain, and therefore, forgery/falsification that may occur in the process of collecting the clinical trial data can be fundamentally prevented, and highly reliable clinical trial data can be collected.

In addition, since personal information is not included in the one-way encryption information that verifies whether or not clinical trial data is forged/falsified, there is no risk of leakage of information on clinical trial subjects, and change history can be managed transparently.

DETAILED DESCRIPTION OF THE PREFERRED EMBODIMENT

Figure 1:
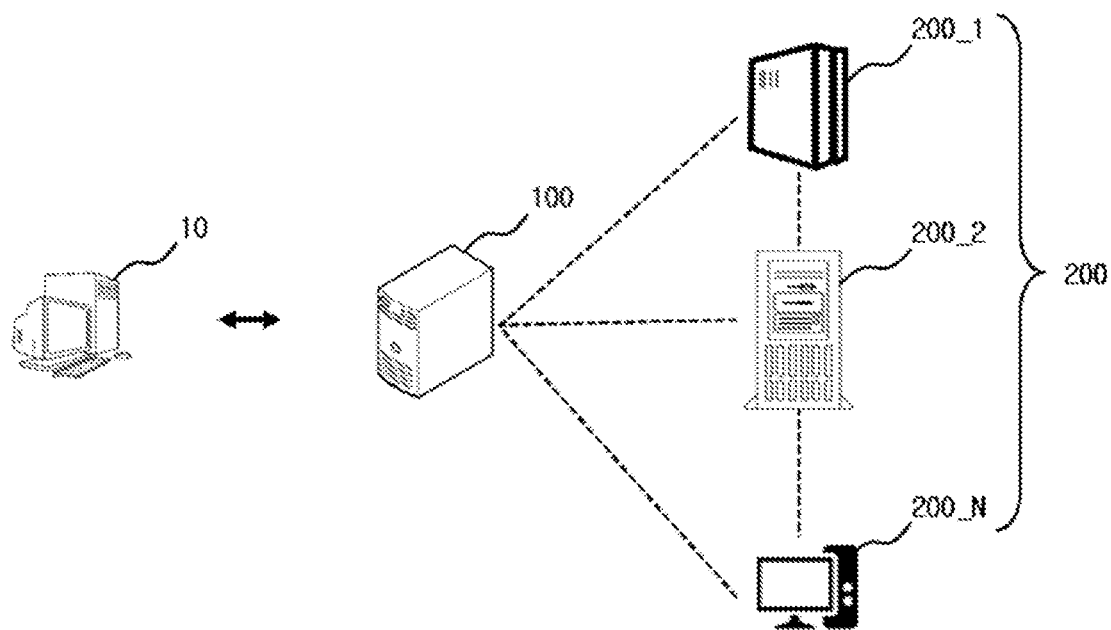
FIG. 1 is a schematic diagram showing a system for collecting clinical trial data based on blockchain according to an embodiment of the present invention.

Hereinafter, preferred embodiments of the present invention will be described in detail with reference to the accompanying drawings in order to clarify the technical spirit of the present invention. In describing the present invention, when it is determined that the detailed description of a related well-known function or component may unnecessarily obscure the subject matters of the present invention, the detailed description thereof will be omitted. Elements having substantially the same functional configuration in the drawings are assigned with the same reference numbers and reference numerals as much as possible even though they are shown in different drawings. For convenience of explanation, the device and method will be described together when needed.

FIG. 1 is a schematic diagram showing a system for collecting clinical trial data based on blockchain according to an embodiment of the present invention.

Referring to FIG. 1, a system for collecting clinical trial data based on blockchain may include a platform 100 and a verification node 200.

The platform 100 may collect clinical trial data based on blockchain. The platform 100 is implemented as a server, and all operations may be performed through an application program, an application, or a web page. When the platform 100 receives the clinical trial data from a researcher terminal 10, it requests verification of the received clinical trial data from a verification node 200, and when a verification result according to the verification request is received, the platform 100 may perform consensus verification on the verification result and propagate the clinical trial data.

Meanwhile, when the platform 100 receives a verification result encrypted with a private key, which is used in an asymmetric key encryption method, from the verification node 200, the platform 100 may confirm the verification result after decrypting it with a public key.

In addition, the platform 100 may set a verification rule of clinical trial data and distribute the verification rule to the verification node 200. Here, the verification rule may include an ID of a case report form and an ID and data value of data to be input as an input value of the clinical trial data, and may include one-way encryption information of the input data as an output value of the clinical trial data. Here, the one-way encryption information means information capable of verifying validity of the input data.

In addition, the platform 100 may have a separate database for storing clinical trial data of which validity has been verified. In addition, the platform 100 may store a plurality of verification rules of the clinical trial data.

The verification node 200 may include one or more nodes such as a first verification node 200_1, and a second verification node 200_2 to an N-th verification node 200_N. Here, the verification node 200 may mean a system connected through a blockchain to verify input clinical trial data by executing the verification rule of the clinical trial data. When the first verification node 200_1, and the second verification node 200_2 to the N-th verification node 200_N receive a verification request from the platform 100, each of the nodes may verify the clinical trial data in the same way.

The verification node 200 may receive and store the verification rule distributed from the platform 100. Accordingly, when the verification request is received, the verification node 200 may verify the clinical trial data by executing the verification rule and return a verification result to the platform 100.

At this point, the verification result may include one-way encryption information of encrypting the clinical trial data only when the clinical trial data is valid. Here, the one-way encryption information may mean a hash value. The hash value is a result value derived by a hash function. The hash function is a function that derives a result of the same length regardless of input data, and the possibility of duplicate derived results is low, and it is difficult to inversely estimate the input value with the result value. For this reason, whether a change has occurred in the data can be grasped by comparing the hash value. SHA-2 (SHA 256) of a form that is more advanced after the Secure Hash Algorithm-1 (SHA-1) is devised first is used as the hash function.

In an embodiment, the verification node 200 may encrypt the verification result with a secret key used in an asymmetric key encryption method and transmit the verification result.

In addition, the verification node 200 may receive the consensus-verified clinical trial data and store the data in each of the one or more nodes such as the first verification node 200_1, and the second verification node 200_2 to the N-th verification node 200_N.

Accordingly, the present invention may fundamentally prevent forgery/falsification that may occur in the process of collecting clinical trial data, and collect highly reliable clinical trial data. Furthermore, since the clinical trial data still remains in a plurality of nodes although the clinical trial data is lost or modified in the platform 100 or some nodes due to hacking or the like, the present invention may continuously and transparently manage the clinical trial data.

This will be described in more detail with reference to FIG. 2.

Figure 2:
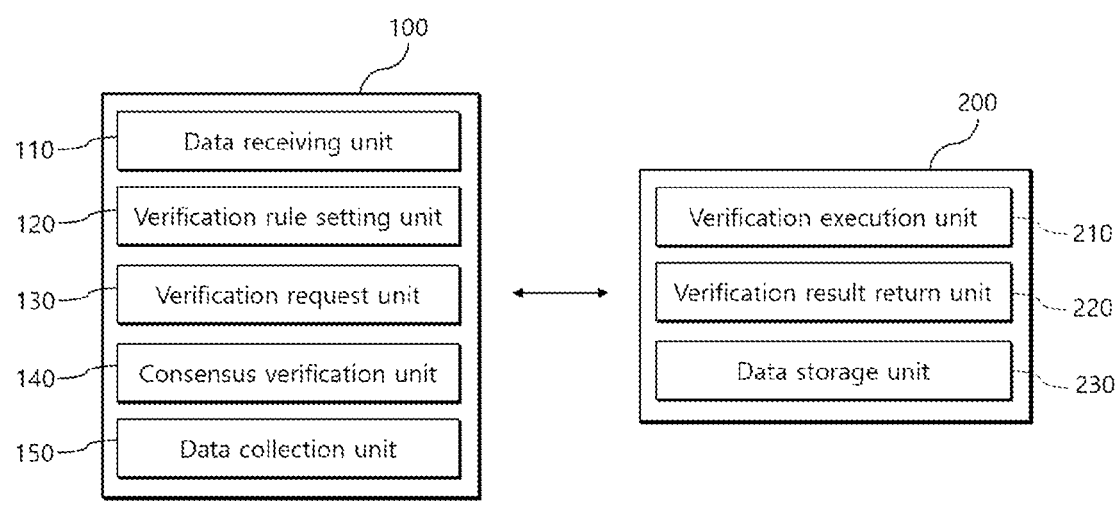
FIG. 2 is a block diagram schematically showing the configuration of a system for collecting clinical trial data based on blockchain according to an embodiment of the present invention.

FIG. 2 is a block diagram showing the configuration of a system for collecting clinical trial data based on blockchain according to an embodiment of the present invention.

Referring to FIGS. 1 and 2, the platform 100 may include a data receiving unit 110, a verification request unit 130, a consensus verification unit 140, and a data collection unit 150. According to embodiments, the platform 100 may further include a verification rule setting unit 120.

The data receiving unit 110 may receive clinical trial data from the researcher terminal 10. That is, the data receiving unit 110 may receive input values for clinical trial data from participants of a clinical trial.

In addition, the data receiving unit 110 may receive a verification result of the verification request from one or more verification nodes 200.

The verification rule setting unit 120 may set a verification rule of clinical trial data and distribute the verification rule to the verification node 200. Here, the verification rule may include an ID of a case report form and an ID and data value of data to be input as an input value of the clinical trial data, and may include one-way encryption information of the input data as an output value of the clinical trial data.

In an embodiment, a pseudocode for the verification rule of clinical trial data may be implemented as "function validate(input)⇒[result: true/false, hash: string]".

In addition, the verification rule setting unit 120 may set the verification rule of clinical trial data in the form of a decision tree.

The verification request unit 130 may request verification by sending the received clinical trial data to one or more verification nodes 200. Thereafter, the verification request unit 130 may receive a verification result of the clinical trial data returned from the one or more verification nodes 200. At this point, when the clinical trial data is valid, the verification result returned from the one or more verification nodes 200 includes a true result value and one-way encryption information of encrypting the result value, whereas when the clinical trial data is invalid, the verification result may include a false result value and an error message.

When a verification result according to the verification request is received, the consensus verification unit 140 may perform consensus verification on the verification result. That is, the consensus verification unit 140 may perform the consensus verification by confirming validity of the one-way encryption information included in the verification result using a blockchain consensus algorithm.

In an embodiment, the consensus verification unit 140 may verify validity of corresponding clinical trial data by comparing one-way encryption information of corresponding clinical trial data returned from the one or more verification nodes, such as the first verification node 200_1, and the second verification node 200_2 to the N-th verification node 200_N, with one-way encryption information set by the verification rule setting unit 120. The consensus verification unit 140 may determine that the clinical trial data is valid when all the one-way encryption information of the clinical trial data returned from the one or more verification nodes 200 match.

In addition, according to the consensus verification result, the consensus verification unit 140 may complete input of the clinical trial data when the clinical trial data is valid or generate an error message when the clinical trial data is invalid.

The data collection unit 150 may propagate consensus-verified clinical trial data to the verification node 200 and collect the consensus-verified clinical trial data. In an embodiment, the data collection unit 150 may propagate information for which the consensus verification is completed to one or more verification nodes 200. That is, the data collection unit 150 may propagate one-way encryption information of the clinical trial data of which validity is confirmed to one or more verification nodes 200. In addition, the data collection unit 150 may collect consensus-verified clinical trial data.

The data collection unit 150 may return a result of transmitting the clinical trial data to the researcher terminal 10. That is, the data collection unit 150 may return a completion message indicating that input of the clinical trial data is complete, or an error message indicating that input of the clinical trial data is failed.

The one or more verification nodes 200 may include a verification execution unit 210, a verification result return unit 220, and a data storage unit 230.

The verification execution unit 210 may verify the clinical trial data by executing the verification rule distributed from the platform 100. Here, the verification rule may vary according to the input value of the clinical trial data. All verification rules may be stored in the data storage unit 230.

An example of the method of executing the verification rule by the verification execution unit 210 will be described.

The verification execution unit 210 performs a verification rule function on the clinical trial data.

if input>80: return [true, generateHash( )];
else return [false, null];

At this point, according to the verification rule that the input value of the clinical trial data should exceed 80, when the input value of the clinical trial data exceeds 80, a true result value and one-way encryption information of encrypting the result value are generated and returned as a verification result.

On the other hand, when the input value of the clinical trial data is 80 or smaller, a false result value and an error message are generated and returned as a verification result.

The verification result return unit 220 may return the verification result of the clinical trial data to the platform 100. Here, the verification result may include the one-way encryption information of encrypting the clinical trial data only when the clinical trial data is valid. In addition, the one-way encryption information may mean a hash value.

That is, when the clinical trial data is valid, the verification result return unit 220 may return a verification result including a true result value and one-way encryption information of encrypting the result value. On the other hand, when the clinical trial data is invalid, the verification result return unit 220 may return a verification result including a false result value and an error message.

Figure 3:
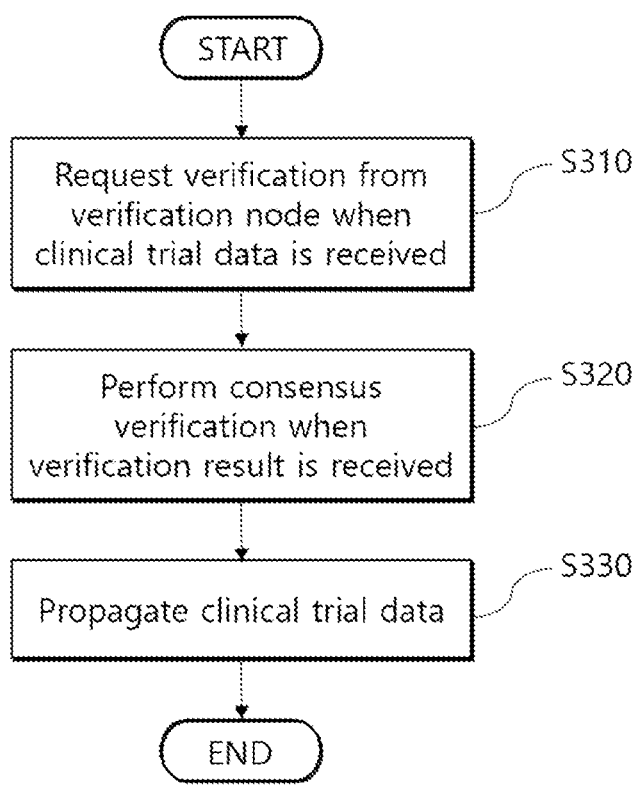
FIG. 3 is a flowchart illustrating a method of collecting clinical trial data based on blockchain in a platform according to an embodiment of the present invention.

FIG. 3 is a flowchart illustrating a method of collecting clinical trial data based on blockchain in a platform according to an embodiment of the present invention.

Referring to FIGS. 1 and 3, in the method of collecting clinical trial data based on blockchain performed in the platform 100, when clinical trial data is received from the researcher terminal 10, verification of the received clinical trial data is requested from one or more verification nodes 200 (S310).

Thereafter, when a verification result according to the verification request is received from the one or more verification nodes 200, consensus verification is performed on the verification result. Here, the consensus verification may mean confirming validity of one-way encryption information according to the verification result using a blockchain consensus algorithm.

Then, according to the consensus verification result, the clinical trial data is propagated to the one or more verification nodes 200 (S330), and the clinical trial data is collected.

An example of a series of steps according thereto will be described.

When a plurality of input fields (CRF, Case Report Form) for inputting clinical trial data is provided through the platform 100, input values of clinical trial data input into each input field may be received from the researcher terminal 10. At this point, a case in which "male" is input in the "gender" field as clinical trial data and the "pregnancy test" field is checked will be described below.

The platform 100 requests verification of the clinical trial data from the one or more verification nodes 200. Accordingly, the verification node 200 performs verification on the clinical trial data by executing the verification rule, and returns a verification result.

Here, the verification node 200 performs a verification rule function on the clinical trial data.

if input={"gender"="male" and "pregnancy test"=true}:
return [false, null];
else return [true, generateHash(A1)];

At this point, according to the verification rule that the "pregnancy test" field of the clinical trial data should be checked when the input value of the "gender" field is "female", when the gender field is "male" and the "pregnancy test" field is checked, a false result value and an error message (Query) are generated and returned as a verification result.

On the other hand, in a case other than the above case, i.e., when the "gender" field is "male" and the "pregnancy test" field is not checked, or when the "gender" field is "female" and the "pregnancy test" field is checked or unchecked, a true result value and one-way encryption information A1 of the result value are returned.

The platform 100 performs consensus verification on the verification result received from the one or more verification nodes 200. Here, the verification result includes a true result value and one-way encryption information A1 of the result value.

Accordingly, the platform 100 performs consensus verification on the clinical trial data according to the verification result using a consensus algorithm. That is, the platform 100 performs verification of validity by comparing the one-way encryption information A1 returned from the one or more verification nodes, such as a first verification node 200_1, and a second verification node 200_2 to an N-th verification node 200_N, with one-way encryption information A1 of the set verification rule. Accordingly, the platform 100 determines that the clinical trial data is valid as the one-way encryption information matches.

As an example of the blockchain consensus algorithm, when the Byzantine Fault Tolerance (BFT) method is used, an input may be determined as a valid input only when ⅔ or more of the one or more verification nodes return a valid verification value (one-way encryption information).

Thereafter, the platform 100 completes input of clinical trial data when the clinical trial data is valid as a result of the consensus verification, and propagates the consensus-verified clinical trial data to the one or more verification nodes 200. At this point, the platform 100 propagates the one-way encryption information A1 of the clinical trial data. Then, the platform 100 returns a result of transmitting the clinical trial data to the researcher terminal 10. The result of transmitting the clinical trial data includes a completion message indicating that input of the clinical trial data has been completed.

Accordingly, as the method of collecting clinical trial data based on blockchain may reject data collection itself when the clinical trial data is not verified at the time point of input, highly reliable clinical trial data can be collected. In addition, there is an advantage in that even when data is lost by hacking in the system itself, the original clinical trial data can be maintained since the clinical trial data are kept in each of the plurality of verification nodes.

Figure 4:
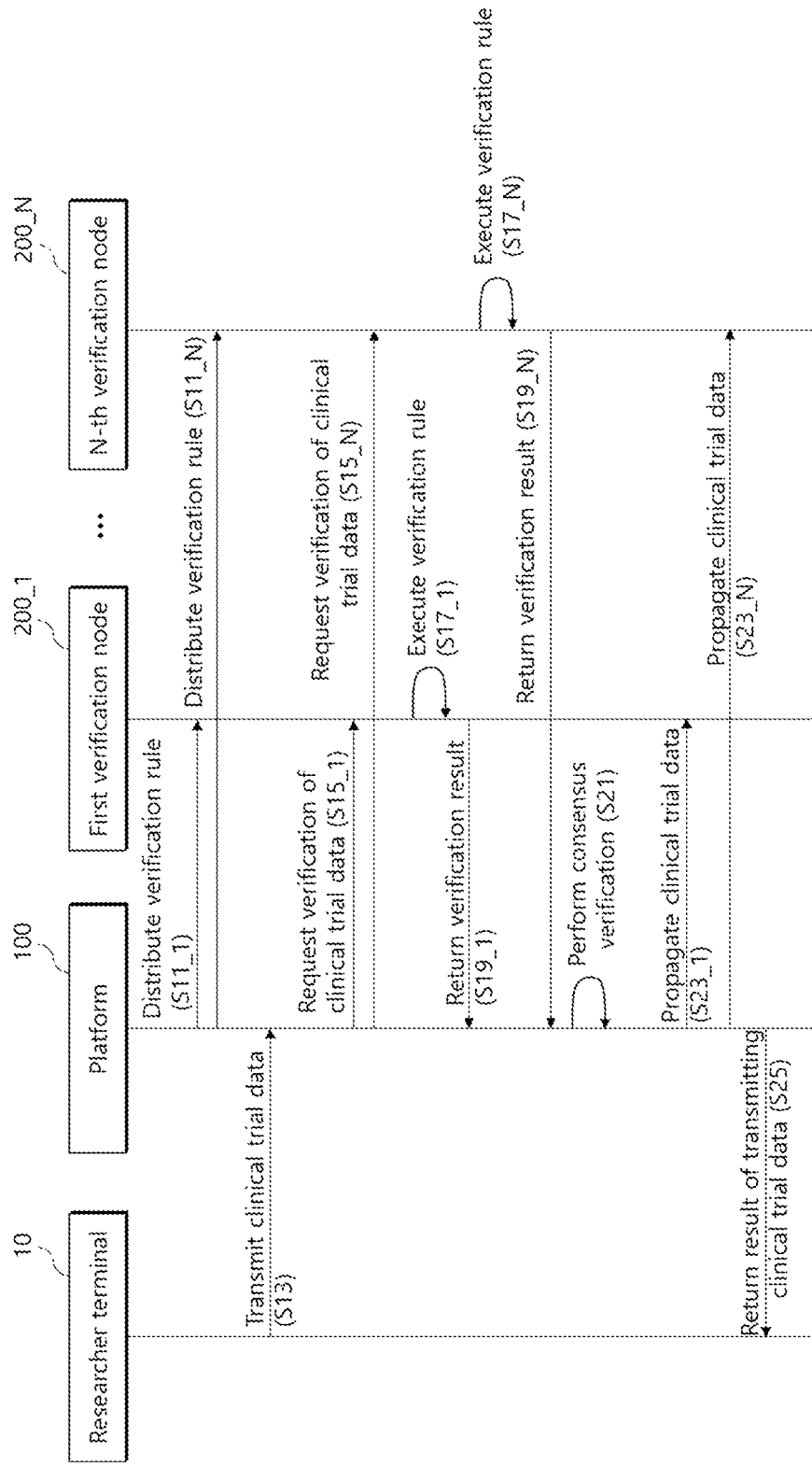
FIG. 4 is a flowchart illustrating a method of collecting clinical trial data based on blockchain according to an embodiment of the present invention.

FIG. 4 is a flowchart illustrating a method of collecting clinical trial data based on blockchain according to an embodiment of the present invention.

Referring to FIGS. 1 and 4, the platform 100 sets a verification rule of clinical trial data, and distributes the verification rule to the first verification node 200_1 to the N-th verification node 200_N (S11_1, S11_N). Here, the verification rule may include an ID of a case report form and an ID and data value of data to be input as an input value of the clinical trial data, and may include one-way encryption information of the input data as an output value of the clinical trial data.

In an embodiment, a pseudocode for the verification rule of clinical trial data may be implemented as "function validate(input)⇒[result: true/false, hash: string]".

The researcher terminal 10 transmits the clinical trial data to the platform 100 through an application program, an application, or a web page (S13).

When the platform 100 receives the clinical trial data from the researcher terminal 10, it requests verification of the received clinical trial data from the first verification node 200_1 to the n-th verification node 200_N (S15_1, S15_N).

The first verification node 200_1 to the n-th verification node 200_N verify the clinical trial data by executing the verification rule distributed from the platform 100 (S17_1, S17_N). Meanwhile, the verification rule may vary according to the input value of the clinical trial data. All verification rules may be stored in each verification node.

An example of the method of executing the verification rule by the first verification node 200_1 to the n-th verification node 200_N will be described.

The first verification node 200_1 to the n-th verification node 200_N perform a verification rule function on the clinical trial data.

if input>80: return [true, generateHash( )];
else return [false, null];

At this point, according to the verification rule that the input value of the clinical trial data should exceed 80, when the input value of the clinical trial data exceeds 80, a true result value and one-way encryption information of encrypting the result value are generated and returned as a verification result.

On the other hand, when the input value of the clinical trial data is 80 or smaller, a false result value and an error message are generated and returned as a verification result.

The first verification node 200_1 to the n-th verification node 200_N may return the verification result of the clinical trial data to the platform 100. Here, the verification result may include the one-way encryption information of encrypting the clinical trial data only when the clinical trial data is valid. In addition, the one-way encryption information may mean a hash value.

The first verification node 200_1 to the n-th verification node 200_N return a verification result including a true result value and one-way encryption information of encrypting the result value when the clinical trial data is valid, and return a verification result including a false result value and an error message when the clinical trial data is invalid (S19_1, S19_N).

Thereafter, the platform 100 receives a verification result of the clinical trial data returned from the first verification node 200_1 to the n-th verification node 200_N. At this point, when the clinical trial data is valid, the verification result returned from the verification node 200 includes a true result value and one-way encryption information of encrypting the result value, whereas when the clinical trial data is invalid, the verification result may include a false result value and an error message.

In addition, the platform 100 performs consensus verification on the verification result (S21). That is, the platform 100 may perform the consensus verification by confirming validity of the one-way encryption information included in the verification result using a blockchain consensus algorithm.

In an embodiment, the platform 100 may verify validity of corresponding clinical trial data by comparing one-way encryption information of corresponding clinical trial data returned from the first verification node 200_1 to the N-th verification node 200_N with one-way encryption information set by the verification rule setting unit 120. The platform 100 may determine that the clinical trial data is valid when all the one-way encryption information of the clinical trial data returned from the first verification node 200_1 to the N-th verification node 200_N match. In addition, according to the consensus verification result, the platform 100 may complete input of the clinical trial data when the clinical trial data is valid or generate an error message when the clinical trial data is invalid.

The platform 100 may propagate consensus-verified clinical trial data to the first verification node 200_1 to the N-th verification node 200_N (S23_1, S23-N) and collect the consensus-verified clinical trial data. That is, the platform 100 may propagate one-way encryption information of the clinical trial data of which validity is confirmed to the first verification node 200_1 to the N-th verification node 200_N. In addition, the platform 100 may collect consensus-verified clinical trial data.

Thereafter, the platform 100 returns a result of transmitting the clinical trial data to the researcher terminal 10 (S25). That is, the platform 100 may return a completion message indicating that input of the clinical trial data is complete, or an error message indicating that input of the clinical trial data is failed.

Until now, the present invention has been described in detail focusing on the preferred embodiments shown in the drawings. These embodiments are not intended to limit the present invention, but are merely illustrative, and should be considered from an illustrative viewpoint rather than a restrictive viewpoint. The true technical protection scope of the present invention should be determined by the technical spirit of the appended claims rather than the above description. Although specific terms are used in this specification, they are only used for the purpose of describing the concept of the present invention and are not used to limit the meaning or scope of the present invention described in the claims. Each step of the present invention does not necessarily need to be performed in the described order, and may be performed in parallel, selectively, or individually. Those skilled in the art will understand that various modifications and equivalent other embodiments are possible without departing from the essential technical spirit of the present invention as claimed in the claims. It should be understood that the equivalents include equivalents to be developed in the future, as well as currently known equivalents, i.e., all elements invented to perform the same function regardless of the structure.

10: Researcher terminal
100: Platform
110: Data receiving unit
120: Verification rule setting unit
130: Verification request unit
140: Consensus verification unit
150: Data collection unit
200: Verification node
210: Verification execution unit
220: Verification result return unit
230: Data storage unit

What is claimed is:

1. A method of collecting clinical trial data based on blockchain, the method comprising:
receiving the clinical trial data from a researcher terminal;
setting a verification rule of the clinical trial data and distributing the verification rule to a plurality of verification nodes;
requesting a verification of the clinical trial data from the plurality of verification nodes;
performing consensus verification on a plurality of verification results when the plurality of verification results according to the verification request is received from the plurality of verification nodes;
propagating the clinical trial data to the plurality of verification nodes based on consensus verification results indicating the clinical trial data is valid, storing the clinical trial data in each of the plurality of verification nodes, and completing input of the clinical trial data;
rejecting the input of the clinical trial data when the consensus verification results indicate that the clinical trial data is invalid,
wherein the clinical trial data includes a plurality of clinical trial data,
wherein the verification of the clinical trial data by the plurality of verification nodes includes consistency between the plurality of clinical trial data input to different fields where to determine mutual contradictory of the clinical trial data,
wherein performing consensus verification on the plurality verification results involves comparing one-way encryption information of the clinical trial data returned from the plurality of verification nodes with the one-way encryption information set by the verification rule to verify the validity of the clinical trial data, and
wherein the verification rule includes an identification (ID) of a case report form and an ID and data value of data to be input as an input value of the clinical trial data, the verification rule including one-way encryption information of an input data as an output value of the clinical trial data.

2. The method according to claim 1, wherein the plurality of verification nodes verifies the clinical trial data by executing the verification rule and returns the verification result.

3. The method according to claim 2, wherein the plurality of verification results include one-way encryption information of the clinical trial data only when the clinical trial data is valid.

4. The method according to claim 3, wherein storing the clinical trial data is rejected when the clinical trial data is not verified at the time point of input.

5. The method according to claim 1, wherein the performing the consensus verification confirms validity of one-way encryption information according to the plurality of verification results using a blockchain consensus algorithm.

6. The method according to claim 5, wherein when Byzantine Fault Tolerance (BFT) method is used, the clinical data is determined as valid clinical data only when ⅔ or more of the plurality of verification nodes return a valid verification value.

7. The method according to claim 1, wherein the one-way encryption information of the clinical trial data excludes personal information.

8. The method according to claim 1, wherein the plurality of verification results are encrypted with a private key, which is in an asymmetric key encryption method from the plurality of verification nodes, and the plurality of verification results are confirmed after decrypting thereof with a public key.

9. A system for collecting clinical trial data based on blockchain, the system comprising one or more processor configured to:
receive the clinical trial data from a researcher terminal;
request verification of the clinical trial data by sending the clinical trial data to the plurality of verification nodes for verification and receive a plurality of verification results of the clinical trial data from a plurality of verification nodes;

establish a verification rule for the clinical trial data and distribute the verification rule to the plurality of verification nodes;

perform consensus verification on the plurality of verification results when the plurality of results are received from the plurality of verification nodes; and propagate a consensus-verified clinical trial data to the plurality of verification nodes and store the clinical trial data in each of the plurality of verification nodes, wherein the clinical trial data includes a plurality of clinical trial data, wherein the verification of the clinical trial data by the plurality of the verification nodes includes verification of consistency to determine whether a plurality of clinical trial data sets for different input fields are mutually contradictory, wherein the consensus verification on the plurality of verification results is configured to perform the input of the clinical trial data if the plurality of verification results indicate that the clinical trial data is valid and reject the input of the clinical trial data if the plurality of verification results indicate the clinical trial data is invalid, wherein the consensus verification on the plurality of verification results is configured to validate the validity of clinical trial data by comparing one-way encryption information returned from plurality verification nodes and the one-way encryption information set by the verification rule, and wherein the verification rule includes an identification (ID) of a case report form and an ID and data value of data to be input as an input value of the clinical trial data, the verification rule including one-way encryption information of an input data as an output value of the clinical trial data.

10. The system according to claim 9, wherein each of the plurality of verification nodes includes:
a verification execution processor configured to verify the clinical trial data by executing the verification rule; and
a verification result return processor configured to return the plurality of verification results of the clinical trial data.

11. The system according to claim 10, wherein the plurality of verification results include one-way encryption information of the clinical trial data only when the clinical trial data is valid.

12. The system according to claim 11, wherein the one or more processors are further configured to perform the consensus verification by confirming validity of the one-way encryption information according to the plurality of verification results using a blockchain consensus algorithm.

13. The system according to claim 9, wherein the plurality of verification nodes further comprises the one or more processor configured to store a plurality of verification rules, and the clinical trial data.

14. The system according to claim 9, wherein the one or more processor returns a result of transmitting the clinical trial data back to the researcher terminal.

15. The system according to claim 9, wherein the one or more processor determines the clinical trial data valid when all the one-way encryption information of the clinical trial data returned from the plurality of verification nodes matches and stores to the one or more processor, wherein if the clinical trial data is invalid, the clinical trial is not stored.

* * * * *